(12) United States Patent
Harabe

(10) Patent No.: US 8,094,926 B2
(45) Date of Patent: Jan. 10, 2012

(54) ULTRAFINE PATTERN DISCRIMINATION USING TRANSMITTED/REFLECTED WORKPIECE IMAGES FOR USE IN LITHOGRAPHY INSPECTION SYSTEM

(75) Inventor: Nobuyuki Harabe, Kanagawa (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 422 days.

(21) Appl. No.: 12/392,545

(22) Filed: Feb. 25, 2009

(65) Prior Publication Data

US 2009/0304262 A1 Dec. 10, 2009

(30) Foreign Application Priority Data

Jun. 6, 2008 (JP) ................................. 2008-148889
Jun. 9, 2008 (JP) ................................. 2008-150072

(51) Int. Cl.
*G06K 9/00* (2006.01)
(52) U.S. Cl. ...................................................... 382/152
(58) Field of Classification Search .................. 382/141, 382/144, 152, 209; 356/237.1–237.6
See application file for complete search history.

(56) References Cited

U.S. PATENT DOCUMENTS

| | | | | |
|---|---|---|---|---|
| 5,795,688 | A * | 8/1998 | Burdorf et al. | 430/30 |
| 6,806,951 | B2 * | 10/2004 | Wack et al. | 356/237.2 |
| 7,590,277 | B2 * | 9/2009 | Oaki et al. | 382/141 |
| 2004/0252296 | A1 * | 12/2004 | Tojo et al. | 356/237.5 |
| 2007/0053583 | A1 * | 3/2007 | Harabe | 382/151 |
| 2007/0064994 | A1 * | 3/2007 | Oaki et al. | 382/144 |
| 2008/0170773 | A1 * | 7/2008 | Wihl et al. | 382/144 |

FOREIGN PATENT DOCUMENTS

| | | |
|---|---|---|
| JP | 8-76359 | 3/1996 |
| JP | 10-97053 | 4/1998 |
| JP | 2004-191957 | 7/2004 |
| JP | 2007-72173 | 3/2007 |
| JP | 2007-72232 | 3/2007 |
| JP | 2007-86534 | 4/2007 |
| JP | 2007-102153 | 4/2007 |
| JP | 2007-310162 | 11/2007 |
| JP | 2008-96296 | 4/2008 |

* cited by examiner

*Primary Examiner* — Michael A Lyons
(74) *Attorney, Agent, or Firm* — Oblon, Spivak, McClelland, Maier & Neustadt, L.L.P.

(57) ABSTRACT

A technique for discriminating a specific pattern, such as an assist pattern, from an integrate circuit pattern of a workpiece by using transmission and reflection images of the workpiece pattern is disclosed. A pattern discrimination device includes an optical image acquisition unit for acquiring a transmissive image of a workpiece having a pattern and a reflective image of the workpiece pattern simultaneously, and a specific pattern detection unit which detects for extraction a specific pattern from among pattern shapes of the transmissive and reflective images in conformity with a distinguishing condition of the specific pattern. A workpiece pattern inspection apparatus using the device is also disclosed.

6 Claims, 12 Drawing Sheets

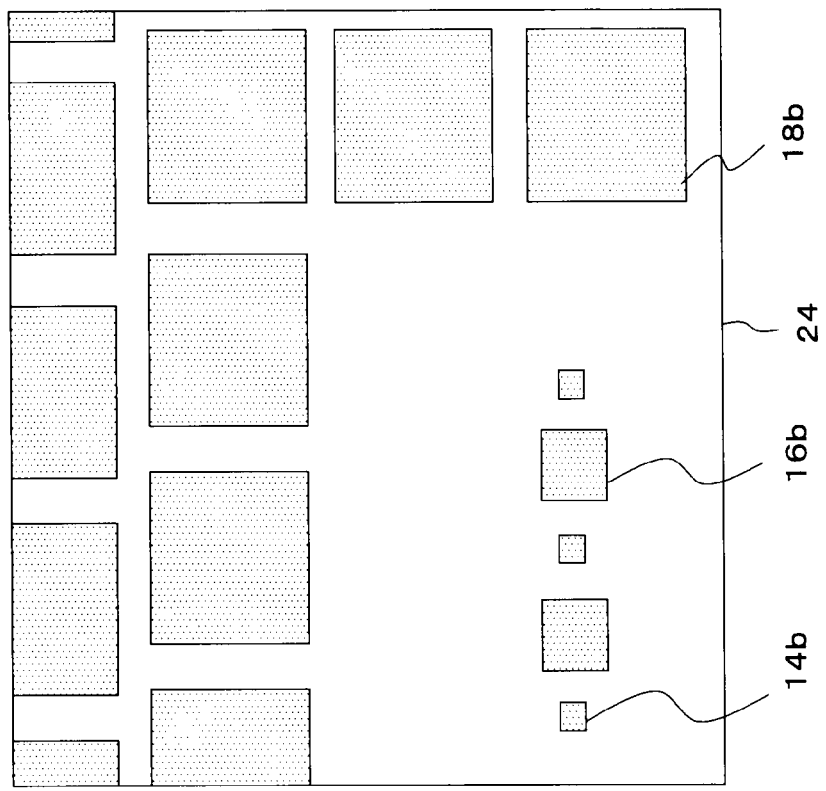
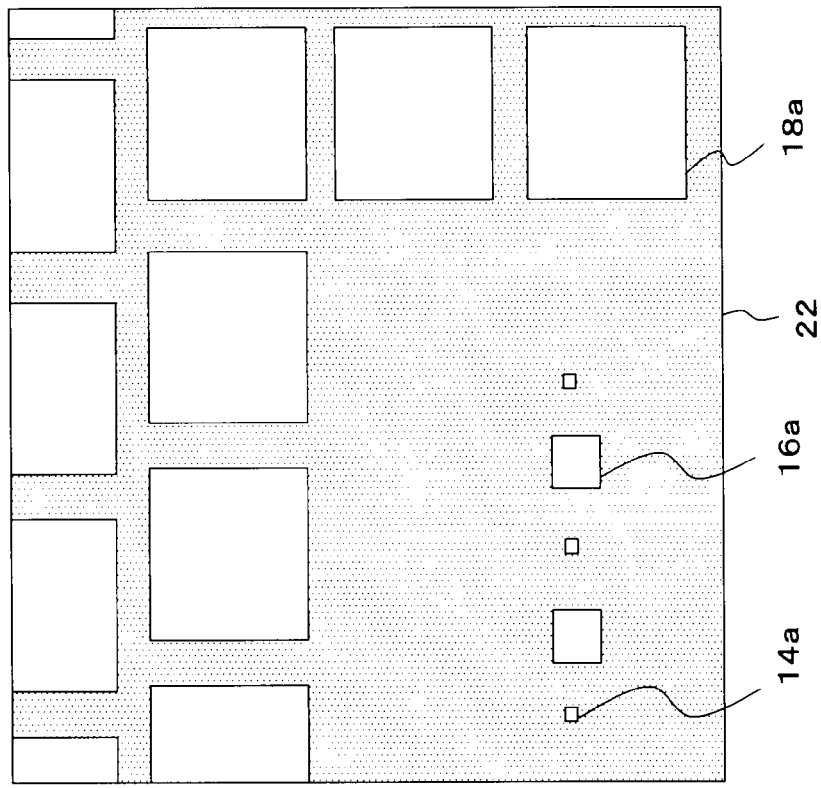

ULTRAFINE PATTERN DISCRIMINATION USING TRANSMITTED/REFLECTED WORKPIECE IMAGES FOR USE IN LITHOGRAPHY INSPECTION SYSTEM

CROSS-REFERENCE TO RELATED APPLICATIONS

Priority is claimed to Japanese Patent Application (JPA) No. 2008-148889, filed Jun. 6, 2008, and to JPA No. 2008-150072, filed Jun. 9, 2008, the contents of which are incorporated herein by reference.

TECHNICAL FIELD

The present invention relates generally to workpiece pattern detection and inspection technologies and, more particularly, to a technique for discriminating and inspecting patterns of workpieces including, but not limited to, photo-masks, wafers or substrates to be used in the process of fabricating semiconductor devices or liquid crystal display (LCD) panels. This invention also relates to workpiece inspection systems using the pattern discrimination/inspection technique.

DESCRIPTION OF RELATED ART

Recent advances in ultralarge-scale integration (ULSI) technology result in feature length and related dimensions of circuit patterns decreasing from the order of submicrons to nanometers. As ULSI circuit patterns shrink in minimum feature size and increase in number of components per chip, the fabrication yield decreases accordingly. One of major causes for such yield reduction is the presence of defects of a photomask, which is used for exposure and transfer of an ultrafine circuit pattern onto semiconductor wafers by photolithography processes. Notably, with the growth in miniaturization of on-wafer ULSI circuitry, pattern defects have become extremely smaller in size to be detected by inspection. This requires higher accuracy of pattern inspection.

Meanwhile, as multimedia technology advances, LCD panels are becoming larger in substrate size and, simultaneously, thin-film transistor (TFT) circuit patterns to be lithographically formed thereon are miniaturized more and more. This trend requires pattern inspection systems to have an ability to check LCD substrates for ultra-small pattern defects extensively at almost every part on large-size substrate surface.

Accordingly, an urgent need is felt to develop a high-accuracy workpiece pattern inspection apparatus capable of efficiently inspecting ultrasmall defects of photomasks in a short period of time. One known approach to attaining this is to perform pattern inspection while varying the inspection accuracy by utilizing features of pattern shapes. Examples of this approach are disclosed in Published Unexamined Japanese Patent Application (PUJPA) Nos. JP 2004-191957A, JP2007-072173A, JP2007-072232A, JP2007-086534A, and JP2007-102153A.

SUMMARY OF THE INVENTION

It is therefore an object of the present invention to provide a technique for discriminating a specific pattern from the pattern of a workpiece under inspection, by using both a transmissive image and a reflective image of the workpiece pattern. Another object of this invention is to optimize the inspection sensitivity with respect to a specific pattern of the workpiece being tested. A further object of the invention is to provide a method and apparatus capable of performing accurate pattern inspection by discriminating an assist pattern from among various pattern components on a workpiece being tested.

To attain the foregoing objects, in accordance with one aspect of this invention, a pattern discrimination device is provided which includes an optical image acquisition unit for acquiring a transmissive image of a workpiece having a pattern and a reflective image of the workpiece pattern substantially simultaneously, and a specific pattern detection unit which detects for extraction a specific pattern from among pattern shapes of the transmissive and reflective images in conformity with a distinguishing condition of the specific pattern.

In accordance with another aspect of the invention, a workpiece inspection apparatus is provided which includes an optical image acquisition unit for acquiring a transmissive image of a workpiece having a pattern and a reflective image of the workpiece pattern substantially simultaneously, a specific pattern detection unit which detects for extraction a specific pattern from among pattern shapes of the transmissive and reflective images in conformity with a distinguishing condition of the specific pattern, a specific inspection execution region setup unit for setting the specific pattern in a specific inspection execution region, and a comparison judgment unit for performing, in the specific inspection execution region, pattern inspection of an optical image acquired by the optical image acquisition unit.

In accordance with a further aspect of the invention, a workpiece inspection apparatus includes an optical image acquisition unit for acquiring both a transmissive image of a workpiece having a pattern and a reflective image of the workpiece pattern at a time, a comparison judgment unit for performing pattern inspection of an optical image acquired by the optical image acquisition unit to thereby extract therefrom a portion which is deemed to be a defect, a specific pattern detection unit for detecting at the portion deemed to be the defect a specific pattern from among pattern shapes of the transmissive and reflective images in a way pursuant to a distinguishing condition of the specific pattern, and a specific inspection execution unit for executing specific inspection if the portion deemed to be the defect is the specific pattern.

In accordance with another further aspect of the invention, a workpiece inspection method includes the steps of acquiring a transmissive image of a workpiece having a pattern and a reflective image of the workpiece pattern substantially simultaneously, and detecting for extraction a specific pattern from among pattern shapes of the transmissive and reflective images in conformity with a distinguishing condition of the specific pattern.

According to the invention as disclosed herein, it is possible to discriminate a specific pattern(s) from among pattern shapes of a workpiece under inspection, by using transmissive and reflective images of the workpiece. It is also possible to optimize the inspection sensitivity relative to the specific pattern of the workpiece. In addition, it is possible to precisely perform the intended pattern inspection by discrimination of one or more assist patterns of the workpiece.

BRIEF DESCRIPTION OF THE DRAWINGS

FIG. 8A is a plan view of a pattern of transmission image of the workpiece; and FIG. 8B is a plan view of a pattern of reflection image.

DETAILED DESCRIPTION OF THE INVENTION

Figure 1:
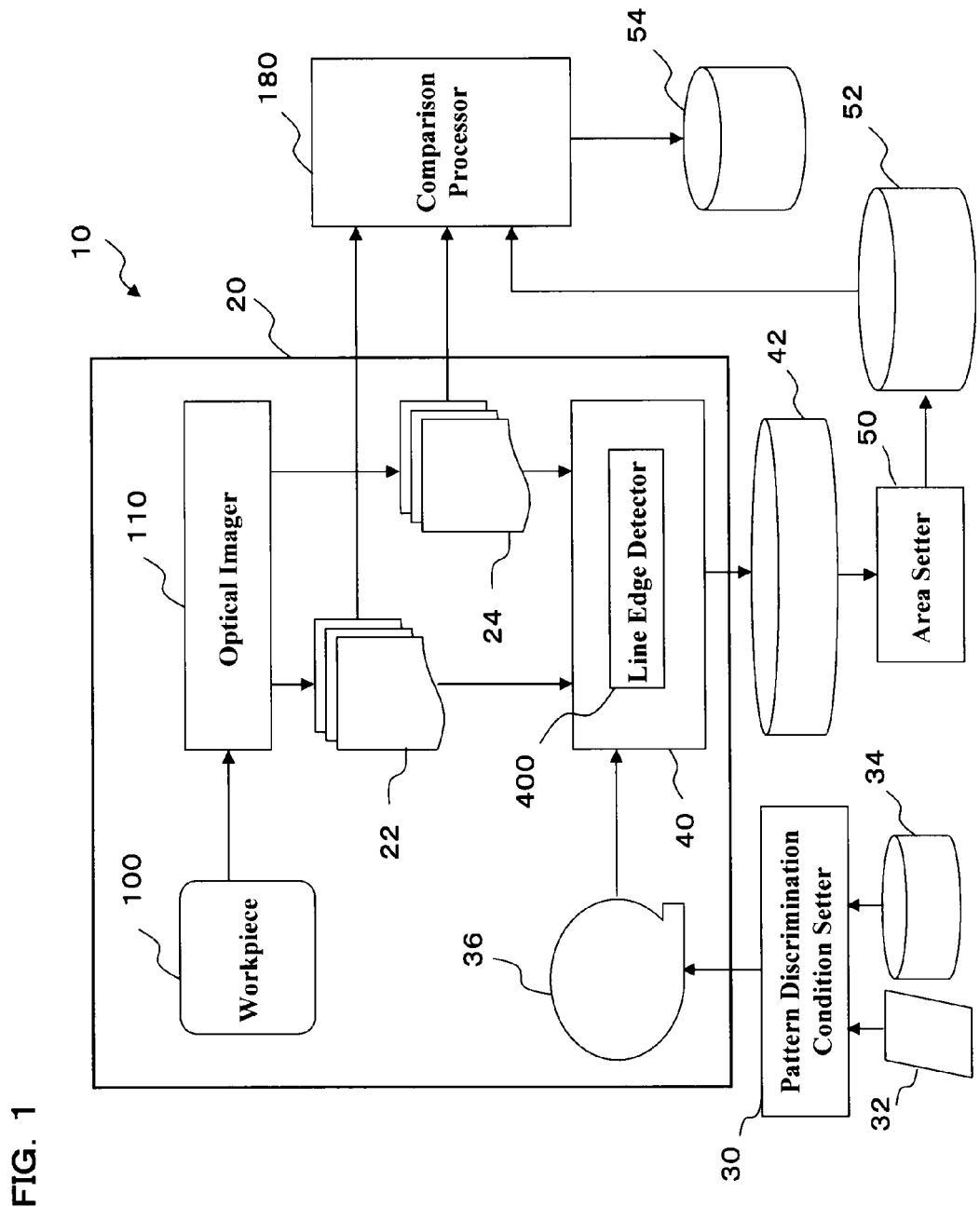
FIG. 1 is a block diagram of a system configuration of a workpiece pattern inspection apparatus in accordance with one preferred embodiment of this invention.

Currently preferred embodiments of this invention will be described with reference to the accompanying figures of the drawing below.

Workpiece Pattern Discrimination Device

Referring to FIG. 1, a workpiece inspection apparatus 10 is shown, which employs a pattern discrimination device 20 in accordance with one embodiment of the invention. The pattern discriminator device 20 includes an optical image acquisition unit 110, which operates to acquire or "capture" two different kinds of optical images—i.e., an image 22 of transmitted light and an image 24 of reflected light—from a highly integrated circuit pattern of a workpiece under inspection. The workpiece may be a photomask, semiconductor wafer, LCD substrate or else. The pattern discriminator 20 also includes a specific pattern detection unit 40, which uses the transmitted image 22 and reflected image 24 along with a specific pattern distinguishing/identifying condition 36 to detect for extraction a specific or "particular" type of pattern or patterns. The specific pattern discrimination condition 36 contains data indicative of optical characteristics of a specific pattern, which data is used to discriminate the specific pattern. The specific pattern is one of circuit pattern components or pattern shapes of the workpiece 100, which needs execution of special processing. For example, in the case of a small-area or thin-line pattern, the transmitted image 22 and reflected image 24 of such pattern appear in the form of pattern images which are different in area from each other. By use of the optical characteristics of these transmitted image 22 and reflected image 24, it becomes possible to detect and identify the specific pattern with no serious fail.

More specifically, the specific pattern is a pattern component which is characterized by its shape and/or size. In the case of rectangular pattern shapes, typical examples of the specific pattern are a contact hole which is one of main patterns of integrated circuitry to be formed on the workpiece, an accessory pattern which is relatively large in size with respect to main patterns and which exists in order to fill a blank space on a photomask, and an assist pattern which is relatively small and which is added to main patterns. The assist pattern functions as an auxiliary of main pattern and is sometimes called the sub-resolution assist feature (SRAF) pattern. Discrimination processing of the specific pattern has the steps of extracting rectangular patterns as candidates for the specific pattern, and, based on size dimensions, dividing them into three groups of specific patterns—i.e., assist patterns, main patterns, and accessory patterns.

For the accessory patterns and assist patterns, inspection with lowered sensitivity is desired, which is called the "desense" inspection. In contrast, for the main patterns such as contact holes, inspection of high sensitivity is required. When size-defined design data is obtainable, such design data may be used. However, if no such data is available, e.g., in the case of die-to-die (DD) pattern inspection, the pattern discrimination technique of this invention is favorably adapted to obtain the size from an optical image(s) to thereby determine which one of detected pattern shapes is the intended specific pattern while distinguishing among assist, main and accessory patterns. Note here that with prior known techniques, whenever an attempt is made to perform inspection with special processing being applied to the specific pattern, it is a must to use an additional data indicating which one of patterns involved is the specific pattern. This results in the inspection being no longer executable in the process of DD inspection and even in the case of die-to-database (DB) inspection if such additional data is not gettable in any way.

One example of the specific pattern determination processing is a method which follows. In the discussion below, a total sum of amounts of light rays that pass through a pattern or rays that are reflected therefrom will be called the "volume." Generally, in an optical system for acquiring both a transmitted image and a reflected image at a time, the ratio R of transmission volume Vt to reflection volume Vr (R=Vt/Vr) varies due to physical phenomena in cases where the pattern size becomes smaller to the extent that is almost equal to the wavelength of an inspection light beam used. This volume ratio change is dependent on the pattern size; so, measuring this change makes it possible to know an approximate value of the pattern size.

The workpiece inspection apparatus 10 shown in FIG. 1 also includes an image comparison determination unit 180 operatively associated with the pattern discriminator device 20. This image comparator 180 is responsive to receipt of the transmitted image 22 and reflected image 24, for comparing them together to generate a comparison result indicating a difference(s) therebetween, if any. This comparison result is used to inspect the workpiece for pattern defects, thereby obtaining inspection result information 54. When doing so, information 52 of a specific inspection execution area containing therein the specific pattern is used to enable execution of more adequate pattern inspection. The specific inspection execution area information 52 is obtainable by a specific inspection execution area setting unit 50 by using specific pattern discrimination information 42, which is gained from the pattern discriminator 20.

The specific inspection is a special kind of processing to be performed for the specific pattern. An example of the special processing is a process of varying the accuracy of pattern inspection—more precisely, increasing or decreasing the inspection accuracy. Another example of the special processing is a process of changing inspection methodology or means, which may be specialized to a certain parameter, such as pattern linewidth, displacement, edge roughness, volume, etc. More precisely, the specific inspection may be the inspection that determines the presence of a pattern defect(s) by examining corresponding patterns to thereby judge whether there is a difference in volume therebetween in the process of comparing optical images for inspection. This inspection is effective in cases where what is primarily required is the sameness of the amount of pattern-passing light while letting a slight difference in pattern shape be ignorable. The above-stated specific inspection execution area setter unit 50 is the one that sets up an area or region for execution of this kind of inspection.

Although the comparison decision unit 180 of FIG. 1 is arranged to use the transmitted image 22 and reflected image 24 to inspect a workpiece for pattern defects, any one of In currently available various comparison methods is employable therefor. Examples of it are comparison of transmitted images together, comparison of reflected images, comparison of either one of the transmitted and reflected images with a referencing image, which is obtained from design data of the circuit pattern transferred onto the workpiece. In such case, the workpiece inspection apparatus 10 performs image comparison using the specific inspection execution area information 52 in a similar way to the case of comparing the transmitted image 22 and reflected image 24.

Figure 2:
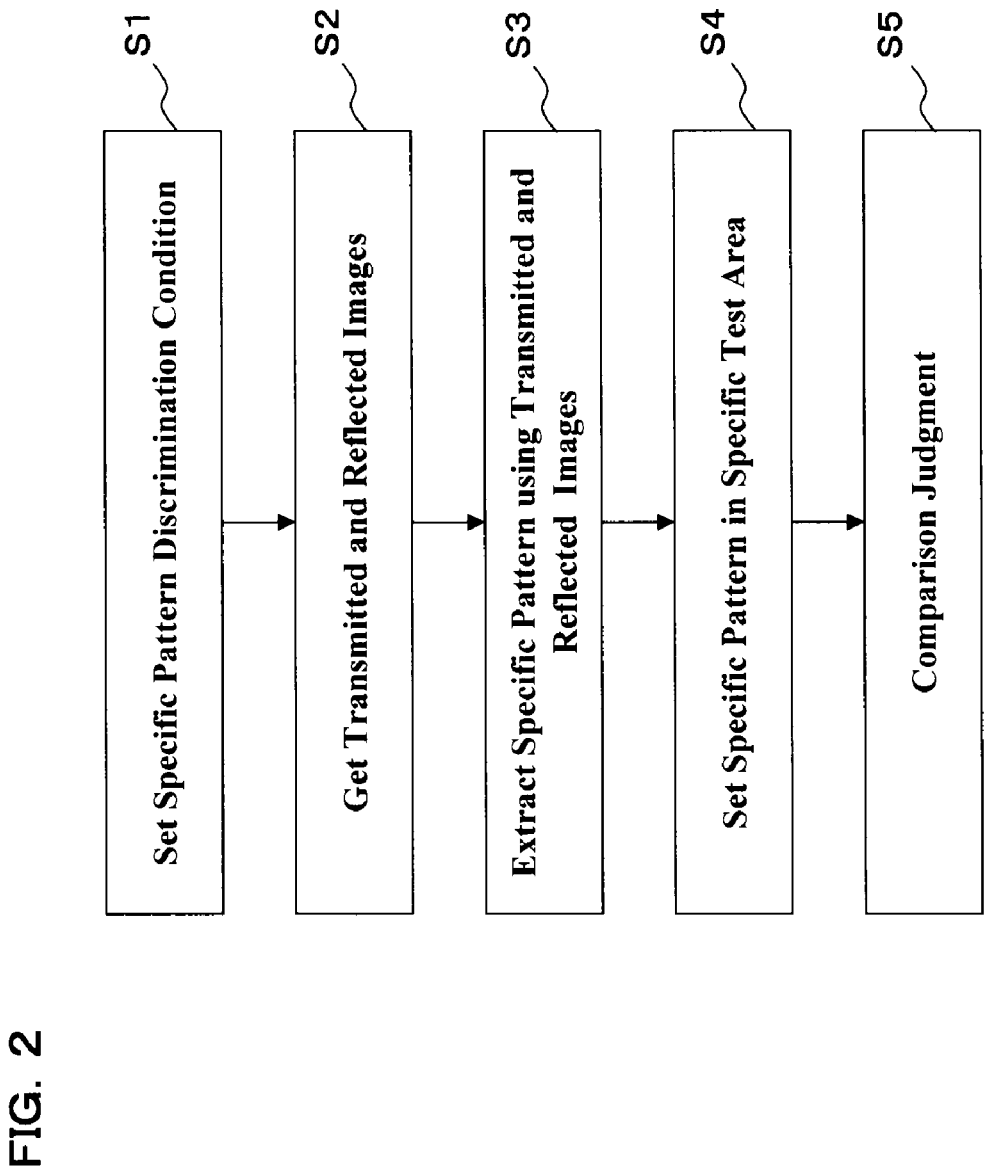
FIG. 2 is a flow diagram of a processing procedure using the workpiece inspection apparatus of FIG. 1.

A procedure of workpiece pattern inspection to be performed by the workpiece inspection apparatus 10 is shown in FIG. 2 in flow diagram form. The pattern inspection process starts with step S1, which causes the specific pattern discrimination condition setter unit 30 to use a representative image 32 and workpiece information 34 to set up the specific pattern discrimination condition 36. In the case of an ensemble of rectangular pattern components as an example, several accessory, main and assist patterns are randomly picked up prior to execution of the workpiece pattern inspection, which are indicated to the inspection apparatus. This apparatus obtains through computation a transmission volume and reflection volume with respect to the individual one of these indicated patterns. Then, it determines boundary conditions, which are border values of such patterns. Next, an intermediate value—say, border volume value—is determined as the threshold for distinguishing between an assist pattern and a main pattern. The intermediate value may typically be a value which is midway between the volumes thereof. Similarly, a border volume value of a main pattern and accessory pattern is determined, which may be an intermediate value between the volumes of these patterns.

Regardless of whether prior to or after completion of the step S1, the system procedure goes to step S2, which causes the optical image acquisition unit 110 to get a transmitted image 22 and reflected image 24 from the workpiece 100 being tested. Then, the procedure goes to step S3 which causes the specific pattern identifier unit 40 to detect and extract the intended specific pattern by using the transmitted image 22 and reflected image 24 plus border volume values. Next, at step S4, the specific inspection execution area setter unit 50 sets the specific pattern in a specific inspection execution area. Lastly, at step S5, the comparison processing unit 180 uses the specific inspection execution area information 52 to perform comparison of the transmitted image 22 and reflected image 24, followed by execution of specific inspection to obtain an inspection result 54 of the workpiece pattern. Very importantly, during the specific inspection at step S5, the inspection accuracy is varied in deference to pattern kinds in a way which follows: the accuracy is decreased or "alleviated" for accessory patterns and assist patterns; the accuracy is increased or "tightened" for main patterns. It should be noted that although in the embodiment of FIG. 1 the specific pattern discrimination condition setter unit 30 is provided external to the pattern discriminator device 20, this unit 30 may alternatively be provided within the pattern discriminator 20 when the need arises.

Figure 3:
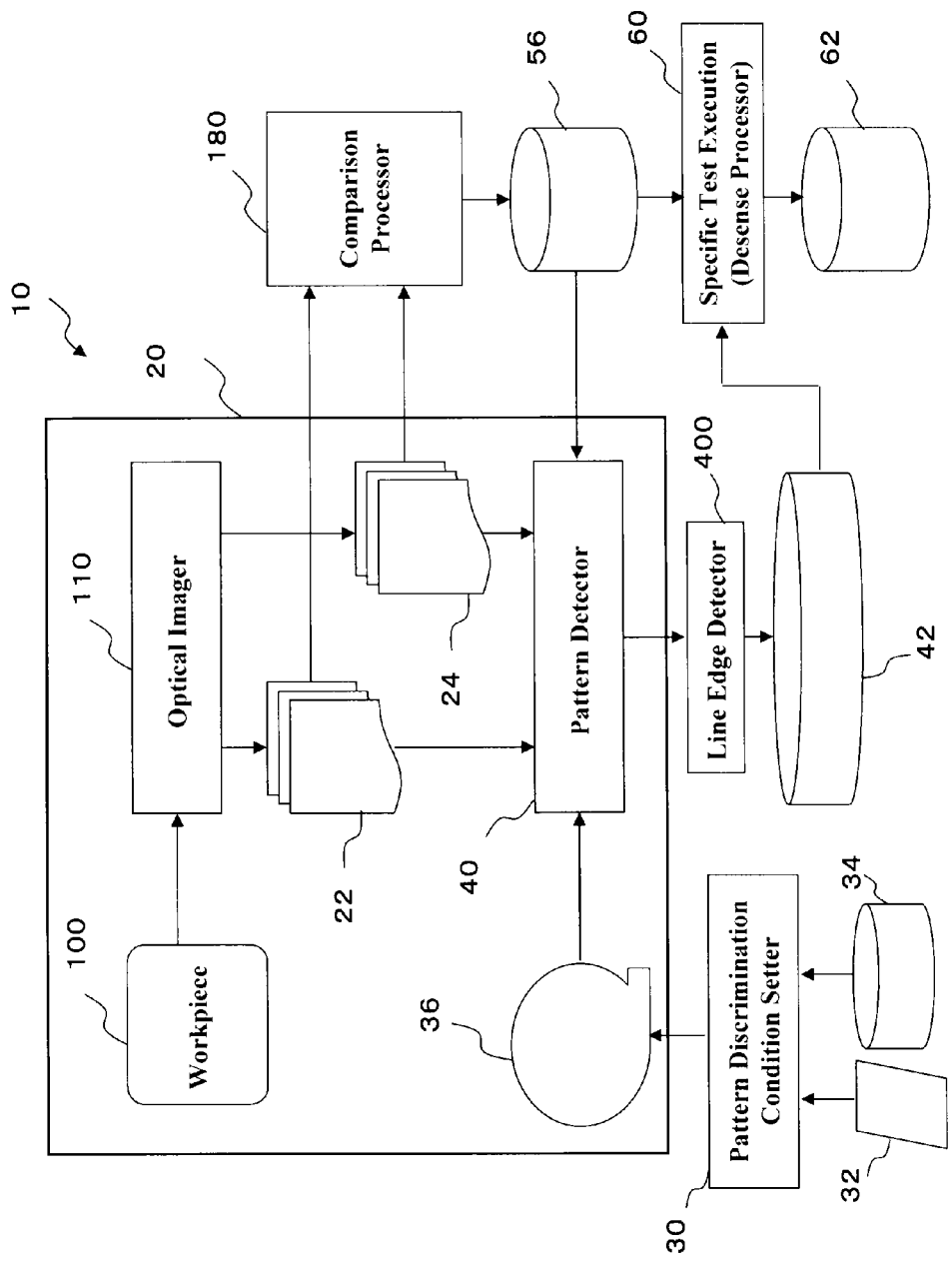
FIG. 3 is a block diagram of a configuration of a workpiece inspection apparatus also embodying the invention.

Referring next to FIG. 3, a workpiece inspection apparatus 10 in accordance with another embodiment of this invention is shown. This apparatus is similar to that shown in FIG. 1 in that it uses the pattern discrimination device 20 but is different therefrom in methodology and means for workpiece pattern inspection. The workpiece inspection apparatus 10 of FIG. 3 compares a transmitted image 22 and reflected image 24 of a workpiece at a comparison decision unit 180 to thereby inspect the workpiece pattern for defects. This inspection is not the final inspection but is the one that is for obtaining provisional inspection result information 56. The pattern discriminator device 20 includes a specific pattern identifier unit 40, which makes reference to the provisional inspection result information 56 and specific pattern discrimination condition 36 for distinguishing a specific pattern(s) from the transmitted image 22 and reflected image 24 to thereby generate specific pattern discrimination information 42. The workpiece inspection apparatus 10 has a specific inspection execution unit 60, which uses the provisional inspection result information 56 and the specific pattern discrimination information 42 to produce deterministic inspection result information 62, which indicates a final inspection result. The workpiece inspection apparatus 10 of FIG. 3 may also be arranged to use currently available various kinds of comparison methods other than the comparison of transmitted image 22 and reflected image 24 in a similar way to the workpiece inspection apparatus 10 of FIG. 1.

Figure 4:
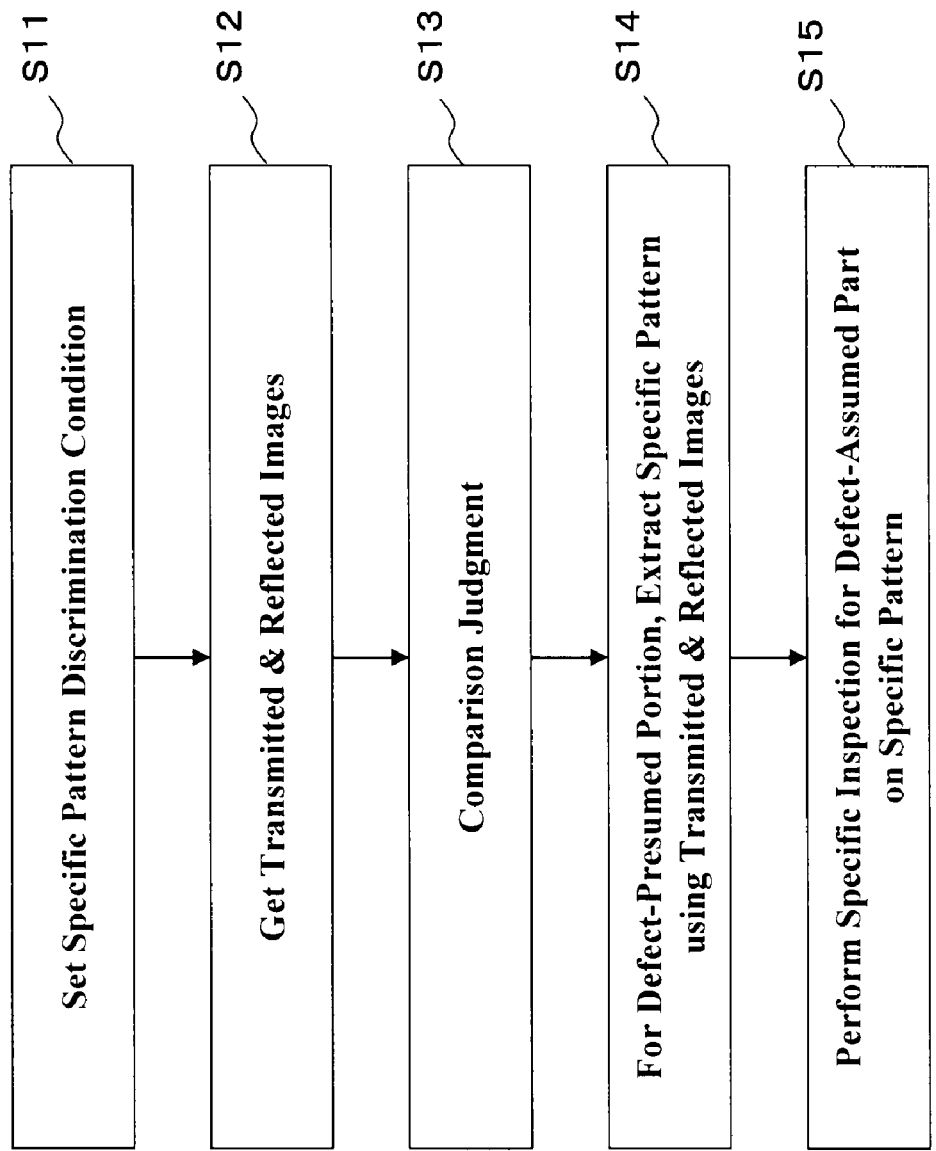
FIG. 4 is a flow diagram of a processing procedure using the workpiece inspection apparatus of FIG. 3.

See FIG. 4, which is a flow diagram of a system routine of workpiece pattern inspection to be performed by the workpiece inspection apparatus 10 of FIG. 3. The workpiece inspection method as shown herein starts with step 11, which causes the specific pattern discrimination condition setter unit 30 to set up specific pattern discrimination condition 36 by use of a representative image 32 and workpiece information 34 in a similar way to the step S1 shown in FIG. 2. Irrespective of whether the process at step S11 is completed or is not started yet, the routine goes to step S12, which causes the optical image acquisition unit 110 to acquire a transmitted image 22 and reflected image 24 from the workpiece 100 being tested. Then, the routine proceeds to step S13, which causes the comparison processor unit 180 to compare the transmitted image 22 and reflected image 24 together to thereby output a provisional inspection result 56 of a portion which is presumed to he a defect of the workpiece pattern. The routine goes next to step S14, which causes the specific pattern identifier unit 40 to use the transmitted image 22 and reflected image 24 along with the specific pattern discrimination condition 36 to create specific pattern discrimination information 42 with respect to the portion that is regarded to be a defect. Lastly, at step S15, the specific inspection execution unit 60 performs specific inspection execution if the defect-deemed portion is on the specific pattern, thereby obtaining deterministic or "final" inspection result information 62.

Configuration of Workpiece Inspection Apparatus

Figure 5:
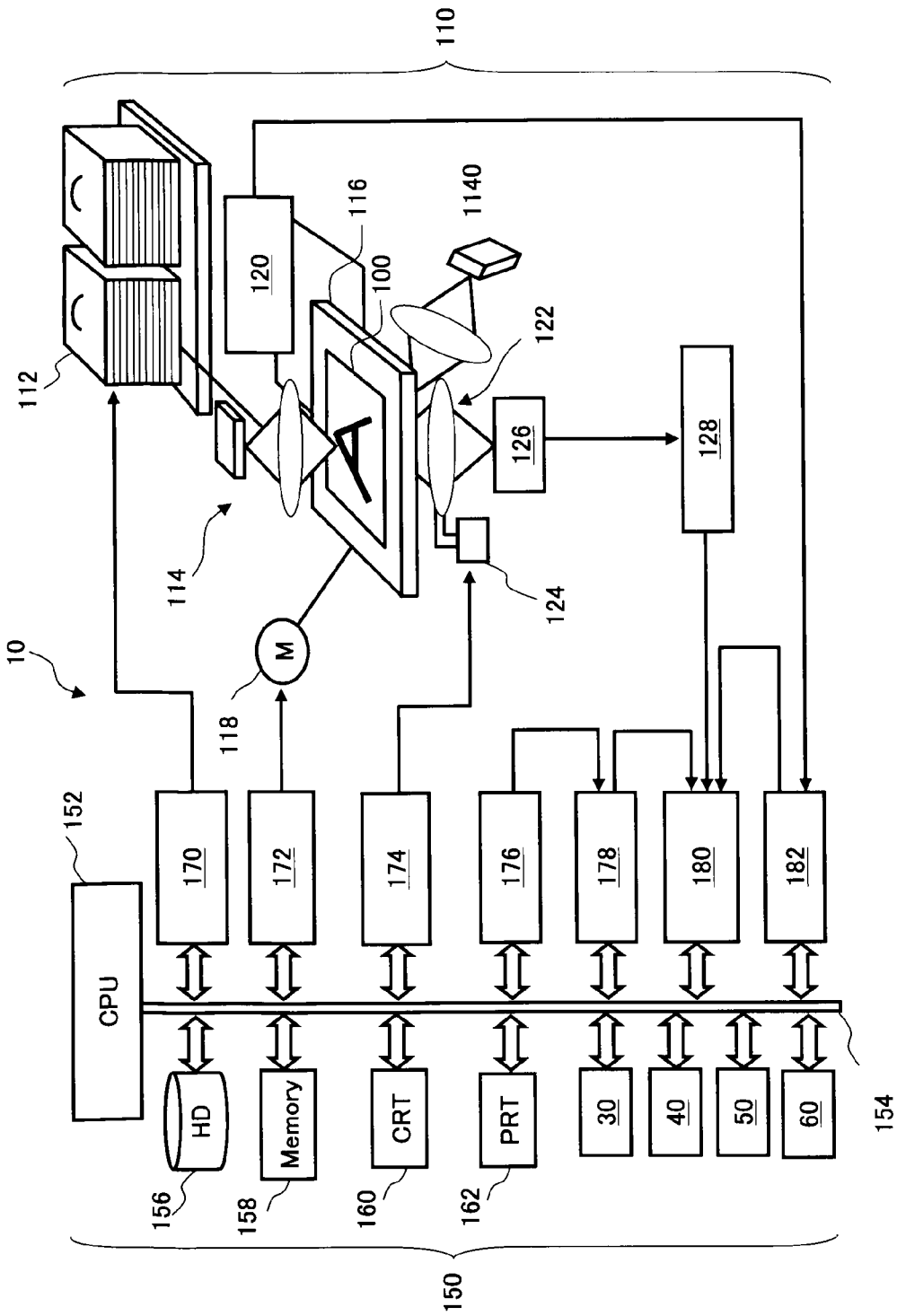
FIG. 5 is a block diagram of an overall configuration of a workpiece inspection apparatus also embodying the invention.

Turning to FIG. 5, an internal configuration of the workpiece inspection apparatus 10 is shown in block diagram form. As previously stated, the workpiece inspection apparatus 10 is the one that inspects a workpiece 100 for pattern defects, wherein the workpiece 100 may be a mask, wafer or substrate. The workpiece inspection apparatus 10 includes optical image acquisition unit 110 and system control unit 150. The optical image acquisition unit 110 is generally made up of an auto-loader 112, an illumination device 114 which produces illumination light of the light passing through the workpiece, i.e., transmission light, an illumination device 1140 which produces illumination light of reflection light, an X-Y-θ table structure 116, a three-axis (XYθ) motor assembly 118, a laser-assisted length measurement system 120, a magnifying optical system 122, a piezoelectric element 124, a photosensing device 126 having a photosensor for receiving transmission light 22 and reflection light 24, such as a charge-coupled device (CCD) image sensor or a photodiode array or the like, and a sensor circuit 128.

The system controller 150 includes a control computer, such as a central processing unit (CPU) 152, which is connected via a bundle of data transfer buses 154 to a large-capacity storage device 156, memory device 158, display device 160, printer device 162, autoloader control unit 170, XYθ table control unit 172, autofocus control unit 174, expander unit 176, referencing unit 178, comparison decision unit 180, position management unit 182, specific pattern discrimination condition setter unit 30, specific pattern identifier unit 40, specific inspection execution area setter unit 50, and specific inspection execution unit 60. The expander unit 176, referencing unit 178, comparison decision unit 180 and position manager unit 182 are linked together as shown in FIG. 5. It is noted that the optical image acquisition unit 110 shown in FIG. 1 or 3 is configurable from the optical image acquisition unit 110 of FIG. 5. Also note that in FIG. 5, those parts other than the constituent components which are necessary for explanation of the embodiment of this invention are omitted from the illustration. The workpiece inspection apparatus 10 is usually designed to include other known parts or components that are required on the case-by-case basis.

Operation of Optical Image Acquisition Unit

The workpiece 100 to be inspected is automatically conveyed from the autoloader 112, which is driven by the autoloader control unit 170, and is then placed on the XYθ table 116. This workpiece 110 has its top surface which is irradiated with illumination light from its upside in order to obtain transmission light. The workpiece 110 has a rear surface which is irradiated with another illumination light from its downside in order to obtain reflection light. Beneath the workpiece 100, the magnifying optics 122 and photosensing device 126 and sensor circuit 128 are disposed. The light that has passed through the workpiece 100, such as a photolithographic exposure mask, travels via the magnifier optics 122 to fall onto the photosensor device 126 to thereby form an optical image thereon. The light that is reflected from the workpiece 100 also travels through magnifier optics 122 to hit the photosensor 126 so that an optical image is formed thereon. In this event, the autofocus control unit 174 controls the piezoelectric element 124 to perform image focusing onto workpiece 100 in order to absorb possible arcuation of workpiece 100 and unwanted variations of XYθ table 116 in Z axis, which is at right angles to X and Y axes.

The XYθ table 116 is driven by the table control unit 172 under control of CPU 152. This table is movable—i.e., horizontally slidable, vertically elevatable, and rotatable about Z axis—with the aid of a drive mechanism, such as the three-axis (X-Y-θ) motor unit 118 having an assembly of X-axis drive motor, Y-axis motor and θ-direction motor. These X-, Y- and θ-motors may be known stepper motors. A moved position of XYθ table 116 is measured by the laser length measurement system 120 on a real-time basis to generate a table position measurement signal, which is supplied to the position manager unit 182. The photosensor device 126 photoelectrically detects a pattern of workpiece 100 to generate at its output electrical image pickup signals each indicating the workpiece pattern. The sensor circuit 128 processes the image signals and then outputs electronic data indicative of optical images sensed—here, a transmitted image 22 and reflected image 24. The transmitted image data and reflected image data as output from the sensor circuit 128 are sent forth toward the comparison decision unit 180, together with the data indicating a present position of the workpiece 100 on XYθ table 116 as output from the position manager unit 182. Additionally, after completion of the pattern inspection, the workpiece 100 on XYθ table 116 is automatically unloaded by autoloader control unit 170. The optical image data may be eight-bit signless data which represents gradation or "tone" levels of the brightness of each pixel.

Figure 6:
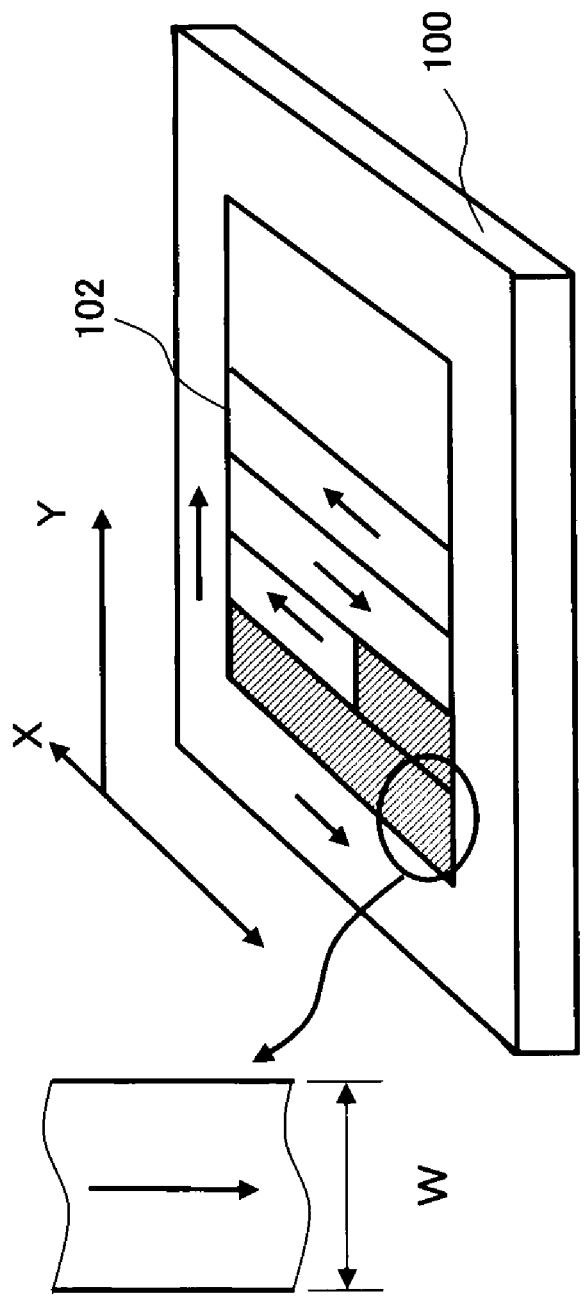
FIG. 6 depicts a perspective view of a workpiece under inspection in the process of acquiring an optical image of a circuit pattern on the workpiece.

As shown in FIG. 6, the workpiece 100 has its surface area to be inspected, which is virtually subdivided in the Y-axis direction by a scan width W. More specifically, the workpiece inspection area is virtually divided into a plurality of strip-like regions 102 each having the scan width W along Y-axis direction. The movement of XYθ table 116 is controlled to ensure that these divided strips 102 are scanned by a beam continuously without any appreciable interruption. The XYθ table 116 is driven to move along X-axis so that the optical image is acquired in units of strips 102. Each strip 102 is a rectangular shape having the scan width W in Y-axis direction and a long-side length extending in X-axis direction as shown in FIG. 6. The light that passed through the workpiece 100 or the light that was reflected therefrom travels via the magnifier optics 122 to enter the photosensing device 126. The photosensor device 126 continuously picks up image segments of strips with the scan width W shown in FIG. 6. After having acquired the image in a first strip 102, the photosensor device 126 continuously inputs the image of a second strip 102 with the scan width W in a similar way, while simultaneously moving in the opposite direction at this time. In the case of acquiring the image of a third strip 103, the photosensor device 126 performs image acquisition while moving in the opposite direction to the image acquisition direction at the second strip 102—that is, in the direction for image acquisition at the first strip 102. Additionally, the scan width W is set at a total length of 2,048 pixels, or more or less, for example.

Producing Reference Image

The design data that was used in the process of pattern formation of the workpiece 100 is stored in the large-capacity storage device 156. The design data is input to the expander unit 176 from large-capacity storage unit 156 under control of CPU 152. In a process of expanding the design data, the expander unit 176 converts the design data of workpiece 100 into two-value (binary) or multi-value original image data. This original image data converted is sent to the referencing unit 178. The referencing unit 178 applies appropriate filtering processing to the original image data to thereby produce a reference image which resembles the optical image. It can be said that the optical image as obtained from the sensor circuit 128 is in the filtered state owing to image resolution properties of the magnifier optics 122 and aperture effects of the photosensor device 126. In this state, there must be found a difference(s) between the optical image and the original image data on the design side; so, filtering is applied by the referencing unit 178 to the original image data on the design side to thereby provide maximal similarity to the optical image.

Specific Pattern Discrimination

Figure 7:
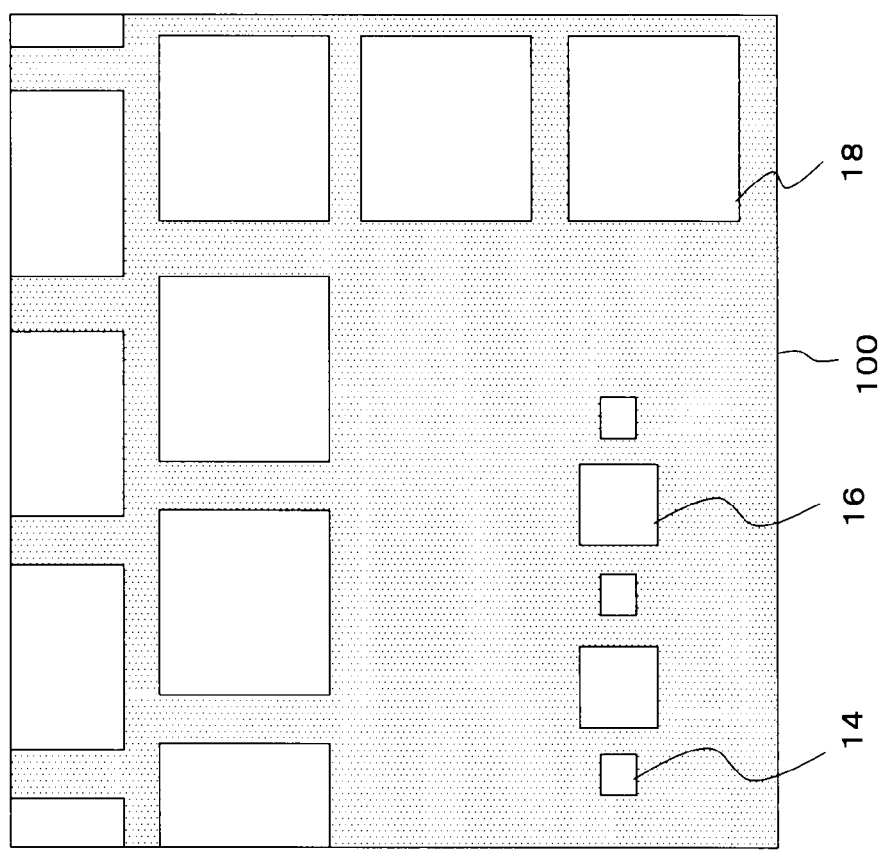
FIG. 7 is a plan view of a cut pattern of a workpiece being tested, which pattern has rectangular open areas being cropped.

FIG. 7 depicts one example of the workpiece 100 having specific patterns of rectangular shapes. As shown herein, workpiece 100 has window-like cutaway portions—called the open area patterns in some cases—of assist patterns 14, main patterns 16 and accessory patterns 18. FIG. 8A shows a transmitted image 22 of an exemplary photomask pattern, which has assist patterns 14a and main patterns 16a plus accessory patterns 18a. FIG. 8B shows a reflected image 24 of the mask pattern having assist patterns 14b, main patterns 16b and accessory patterns 18b.

For each of the assist patterns 14a-14b, main patterns 16a-16b and accessory patterns 18a-18b of the transmitted and reflected images shown in FIGS. 8A-8B, the volume ratio R of a transmission volume Vt to reflection volume Vr (R=Vt/Vr) is calculated. Calculation results are as follows: for the accessory pattern 18, R=1; for main pattern 16, R=0.6; for assist pattern 14, R=0.25.

Note here that prior to execution of the pattern inspection, an appropriate number of ones are randomly preselected from the assist patterns 14, main patterns 16 and accessory patterns 18, respectively, to determine in advance a border volume ratio Rth1, which is used as a threshold for discrimination between an accessory pattern and a main pattern. The accessory/main pattern threshold volume ratio Rth1 is set at 0.8, for example. Also computed before the inspection is a threshold volume ratio Rth2 for discrimination between a main pattern and assist pattern. This main/assist pattern threshold volume ratio Rth2 is set to 0.4 as an example. Using these threshold volume ratios Rth1 and Rth2 makes it possible to accurately detect and distinguish any one of the assist, main and accessory patterns from the others in a way which follows. If a target pattern shape is detected to have its volume ratio R which is above the threshold Rth1=0.8, this pattern is determined to be one of the accessory patterns. If the target pattern has its volume ratio R which falls within a range of from Rth1=0.8 to Rth2=0.4, it is decided to be a main pattern. If the target has a volume ratio R below Rth2=0.4 then it must be an assist pattern.

While the specific pattern discrimination technique incorporating the principles of this invention has been stated in terms of a workpiece having the cut pattern shown in FIG. 8A, this specific pattern discrimination technique is also applicable to a workpiece having the residue or "remainder" pattern shown in FIG. 8B—this is the reversal to the cut pattern—by predefining prior to the inspection the accessory/main and main/assist threshold volume ratios Rth1 and Rth2 in a similar way to that stated supra.

Below is a detailed explanation of a method and means for discriminating assist patterns in the specific patterns. For the purpose of explanation, the reference characters as used in the foregoing figures of the drawing will be handled so that these are limited to assist patterns in a way which follows. The above-stated pattern discrimination device 20 shown in FIG. 1 or 3 will be interpreted hereinafter as an assist pattern discriminator device 20; the specific pattern discrimination condition 36 is deemed hereafter as an assist pattern discrimination condition 36; the specific pattern discrimination condition setter unit 30 is read as an assist pattern discrimination condition setter unit 30; the specific pattern identifier unit 40 is as an assist pattern identifier unit 40; the specific pattern discrimination information 42 as assist pattern discrimination information 42; the specific inspection execution area setter unit 50, a desense area setter unit 50; the specific inspection execution area information 52, desense area information 52; and, the specific inspection execution unit 60, a desense processing execution unit 60.

Assist Pattern Discrimination Device

As shown in FIG. 1, a workpiece inspection apparatus 10 includes an assist pattern discrimination device 20 in accordance with an embodiment of this invention. The assist pattern discriminator 20 is equipped with an optical image acquisition unit 110 for acquiring a transmitted image 22 and reflected image 24 from the pattern of a workpiece 100 being tested, such as a photomask, wafer or LCD substrate or else, and an assist pattern identifier unit 40 for detecting for extraction an assist pattern(s) by using the transmitted image 22 and reflected image 24 along with assist pattern discrimination condition 36. The assist pattern identifier 40 has a line edge determination unit 400 for detecting and identifying edges of an assist pattern in order to obtain the region of a tip end portion of the assist pattern, which is required especially for execution of the "desense" processing, i.e., pattern detection sensitivity decreasing processing as stated supra. The line edge finder 400 may alternatively be disposed at locations other than inside of the assist pattern identifier 40. For example, edge finder 400 may be connected at a subsequent stage of assist pattern identifier 40.

With prior art techniques, when an attempt is made to perform workpiece pattern inspection while applying the desense processing to assist patterns, it is inevitable to use additional data indicating which one of pattern components is the assist pattern. By contrast, with the embodiment of this invention, it becomes possible to perform, without use of such additional data, the intended desense inspection by discriminatorily finding the individual assist pattern from among many pattern shapes in an optical image of workpiece being tested.

The workpiece inspection apparatus 10 includes, in addition to the assist pattern discriminator device 20, a desense area setting unit 50, comparison processing unit 180 and assist pattern discrimination condition setter unit 30. The desense area setter 50 uses the assist pattern discrimination information 42 that is issued from the assist pattern discriminator device 20 to generate desense area information 52 of a desense area which contains the assist pattern. The comparison decision unit 180 compares the transmitted image 22 and reflected image 24 together for inspecting the workpiece pattern for defects, thereby to provide inspection result information 54. When doing so, for the assist pattern-containing desense area indicated by information 52, the pattern defect detection sensitivity is lowered to permit execution of more adequate pattern inspection with respect to the defect detection-required pattern. The assist pattern discrimination condition setter unit 30 uses a representative image 32 and workpiece information 34 to set up assist pattern discrimination condition 36. Although in FIG. 1 the assist pattern discrimination condition setter 30 is provided external to the assist pattern discriminator device 20, this condition setter 30 may alternatively be provided within the assist pattern discriminator 20.

Figure 9:
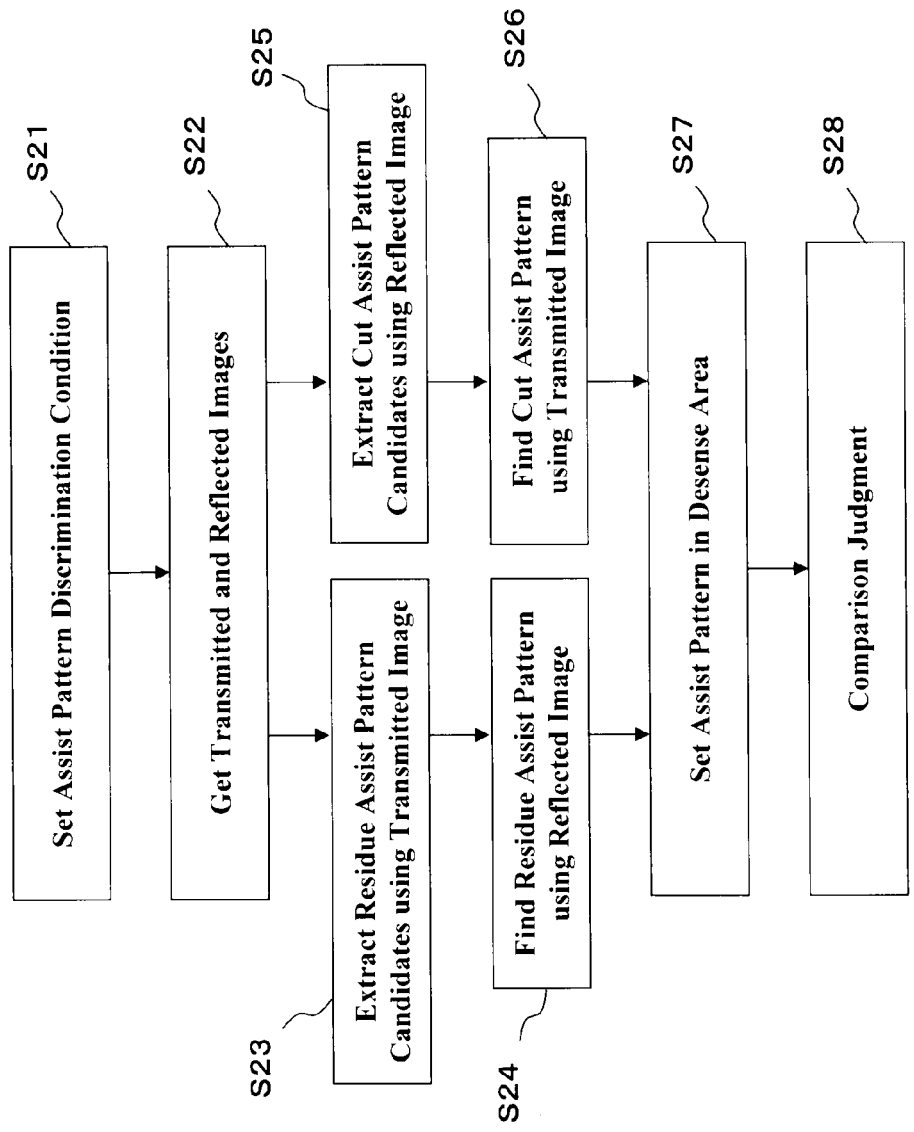
FIGS. 9 and 10 are flowcharts of other processing procedures, wherein the former uses the workpiece inspection apparatus shown in FIG. 1 whereas the latter uses the apparatus of FIG. 3.

See FIG. 9, which shows a system procedure for workpiece pattern inspection including the assist pattern discrimination process that is performed by the workpiece inspection apparatus 10 of FIG. 1. The assist pattern discrimination starts with step S21, which causes the assist pattern discrimination condition setting unit 30 to use the representative image 32 and workpiece information 34 to set up assist pattern discrimination condition 36. Irrespective of whether a present process state is before or after the step S21, the procedure goes to step S22 which causes the optical image acquisition unit 110 to acquire from a workpiece 100 under inspection both a transmitted optical image 22 and reflected image 24 at a time.

In a case where the workpiece pattern is a residual or "remainder" pattern, the system procedure goes next to step S23, which causes the assist pattern identifier unit 40 to utilize the assist pattern discrimination condition 36 to extract residual assist pattern candidates by use of the transmitted image 22; then, go to step S24 which performs discrimination of one or more assist patterns using the reflected image 24 with respect to the residue assist pattern candidates extracted. Alternatively, in case the workpiece pattern is a cut pattern, the system routine proceeds to step S25, which causes the assist pattern identifier 40 to extract candidates for cut assist patterns using the reflected image 24; then, go to step S26 which performs discrimination of more than one cut assist pattern using the transmitted image 22 with respect to the cut assist pattern candidates.

Note here that the workpiece of residue pattern is a workpiece which is made of a substrate with those portions other than opaque patterns being optically transparent. An example of it is a photomask which has a transparent substrate with a surface on which opaque patterns are formed or "drawn." On the contrary, the workpiece of cut pattern is a workpiece which is made of a substrate with those portions other than transparent patterns being opaque. An example of it is a photomask that has an opaque substrate with transparent patterns being formed thereon. Note here that the term "transparent" denotes to have the property of transmitting light rays falling onto a workpiece being tested whereas the term "opaque" refers to exhibiting optical opacity for blocking or hindering the passage of light rays illuminating the test workpiece.

In the above-stated assist pattern discrimination processing, the discrimination condition that allows an image change due to the size of a transmitted image to become greater than an image change of reflected image is used exclusively for the cut assist patterns. On the other hand, for the residual assist patterns, another discrimination condition is used, which causes an image change due to the size of a reflected image to be larger than that of transmitted image. The discrimination condition is such that the size ratio of the transmitted image of an assist pattern versus the reflected image thereof becomes larger in value as the assist pattern becomes smaller in size and narrower in line width. In other words, the smaller the size of a cut assist pattern, the less the size of a transmitted image of this pattern relative to its reflected image. As for a residual assist pattern, the smaller the size of this assist pattern, the greater the size of its transmitted image relative to reflected image.

At step S27 in the flowchart of FIG. 9, the desense area setter unit 50 sets the extracted assist pattern in a desense area on the workpiece surface. Lastly, at step S28, the comparison processor unit 180 uses the desense area information 52 to compare the transmitted image 22 and the reflected image 24 together to thereby obtain an inspection result of the workpiece pattern. In this process of comparison judgment, the sensitivity of inspection in the desense area is lowered when compared to the inspection sensitivity in areas of those pattern shapes which require execution of high accuracy inspection. It should be noted that although at step S28 the transmitted image 22 and reflected image 24 are used to inspect the workpiece pattern for defects, other known various comparison methods are employable therefor. Examples of such methods include comparison of transmitted images together, comparison of reflected images, and comparison of an optical image (transmitted or reflected image) with a referencing image which is obtained from master design data of the workpiece pattern.

A workpiece inspection apparatus 10 is shown in FIG. 3, which is similar to that shown in FIG. 1 in use of the assist pattern discrimination device 20 but is different therefrom in methodology and means for workpiece pattern inspection. The workpiece inspection apparatus 10 of FIG. 3 includes an assist pattern discriminator device 20, desense processing execution unit 60, comparison processor unit 180, assist pattern discrimination condition setting unit 30 and others. The comparison processor 180 compares a transmitted image 22 and reflected image 24 together to inspect a workpiece pattern for defects. This inspection is not the final inspection but provisional inspection for obtaining provisional "temporary" inspection result information 56.

The assist pattern discriminator device 20 includes an assist pattern identifier unit 40 which makes reference to the provisional test result information 56 and assist pattern discrimination condition 36 to detect and extract assist patterns from the transmitted image 22 and reflected image 24 to thereby obtain assist pattern discrimination information 42. When doing so, a line edge deciding unit 400 is rendered operative to find line edges or ends of the assist patterns and then generates data indicative of these detected line edges, which data is included in the assist pattern discrimination information 42. The assist pattern identifier unit 40 obtains those portions which are presumed to be pattern defects based on the provisional test result information 56 and then performs extraction of assist pattern candidates and/or assist pattern discrimination with respect to these defect-presumed portions.

The desense processing execution unit 60 uses the provisional test result information 56 and assist pattern discrimination information 42 to obtain deterministic inspection result information 62, which is a final test result of the workpiece pattern. In the process of performing comparison inspection, the desense processing execution unit 60 forces the sensitivity of pattern inspection to be lowered at those locations whereat the defect-presumed portions correspond to assist patterns.

Figure 10:
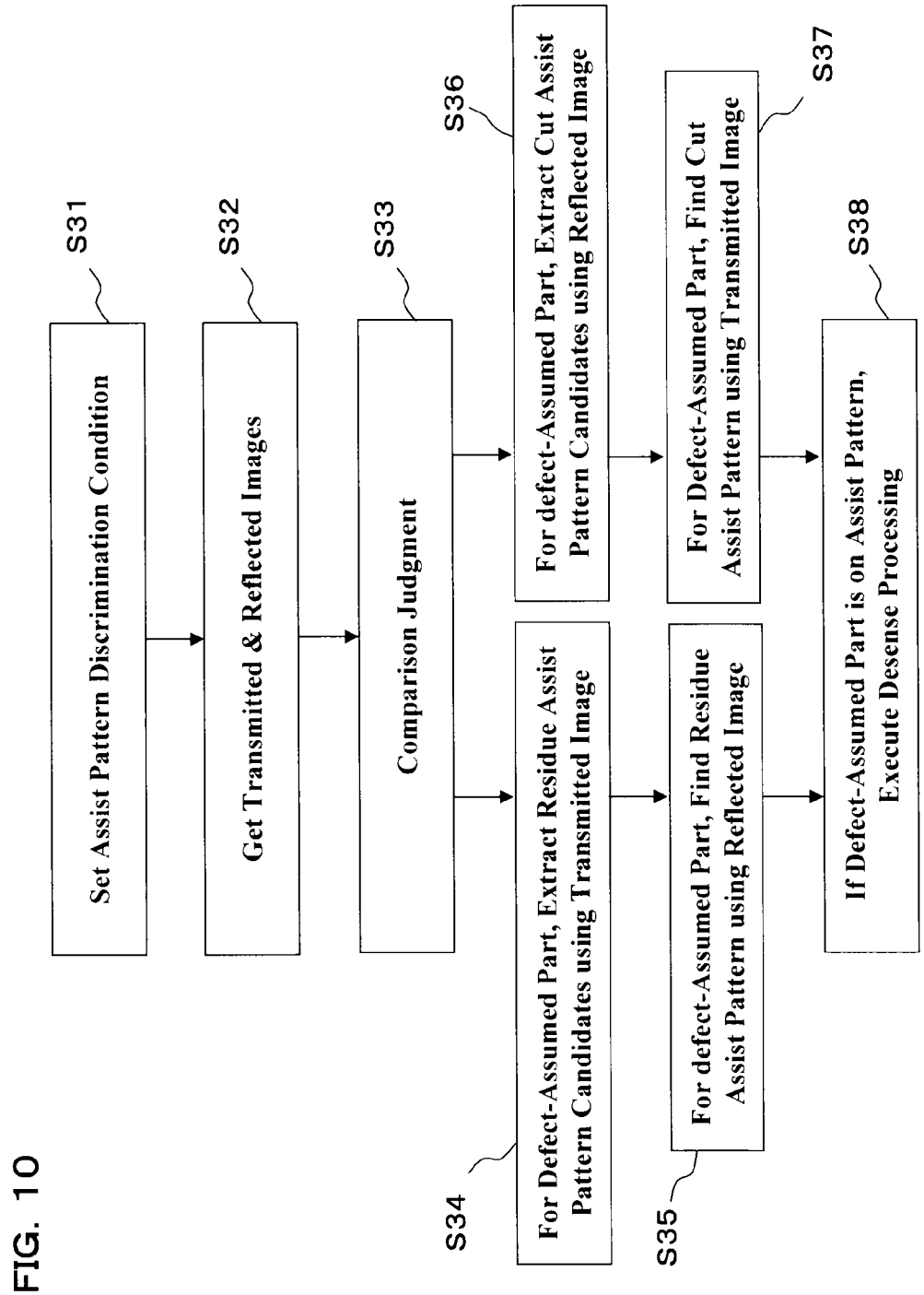

Turning to FIG. 10, a procedure of workpiece pattern inspection method relating to the workpiece inspection apparatus 10 is shown. The workpiece inspection starts with step S31, which causes the assist pattern discrimination condition setter unit 30 to use a representative image 32 and workpiece information 34 to set up assist pattern discrimination condition 36. Irrespective of whether a present process state is before or after the step S31, the procedure goes to step S32, which causes the optical image acquisition unit 110 to acquire both a transmitted image 22 and reflected image 24 at a time. Then, at step S33, the comparison processor unit 180 performs comparison judgment of the transmitted image 22 and reflected image 24 to thereby obtain a provisional inspection result 56 of a portion or portions which are presumed to be defects of the workpiece pattern 12 being tested. Note here that at the step S33, various kinds of currently available comparison methods other than the comparison of transmitted image 22 and reflected image 24 may be utilized in a similar way to the process at step S28 of FIG. 9.

Next, the defect-presumed portions are applied the following processing. In case the workpiece pattern is a residue pattern, the procedure goes to step S34, which causes the assist pattern identifier unit 40 to perform extraction of residual assist pattern candidates using the transmitted image 22 with respect to the defect-presumed portions, and goes next to step S35 which performs discrimination of residue assist patterns using the reflected image 24 with respect to the defect-presumed portions. In case the workpiece pattern is a cut pattern, the procedure goes to step S36, which causes the assist pattern identifier 40 to perform extraction of cut assist pattern candidates using the reflected image 24 with respect to the defect-presumed portions; then, go to step S37 which performs discrimination of cut assist patterns using the transmitted image 22 with respect to the defect-presumed portions. In this processing also, an assist pattern discrimination condition similar to that in the procedure of FIG. 2 is used. Lastly, at step S38, the desense processing execution unit 60 applies desense processing to certain ones of the defect-assumed portions which are on the assist patterns, thereby generating final inspection result information 62.

Assist Pattern Discrimination

Figure 11B:
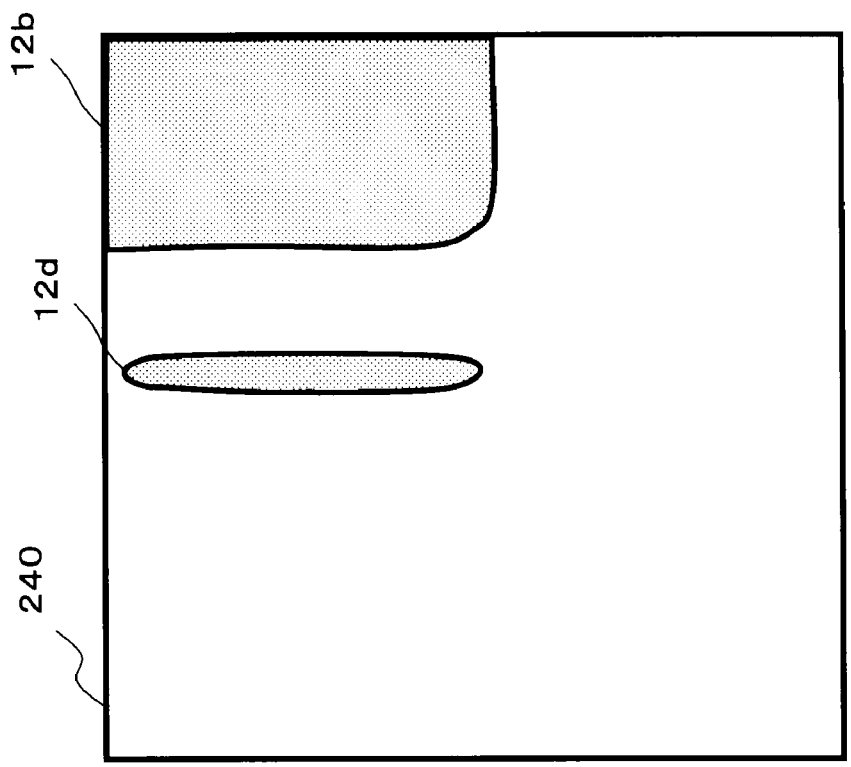
FIG. 11B shows a pattern of reflection image in case the workpiece pattern is a cut pattern.
Figure 11A:
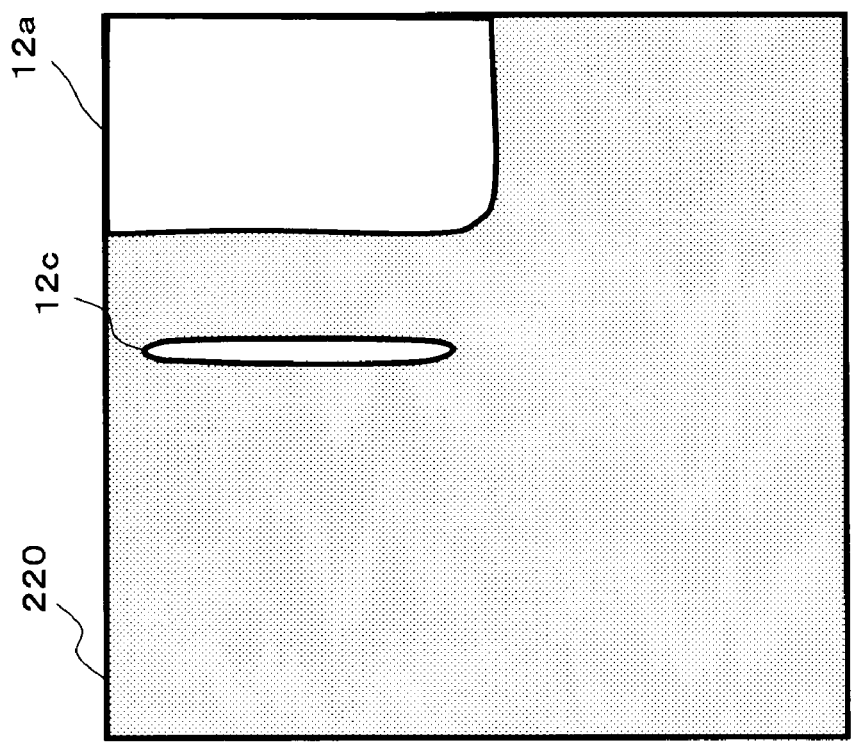
FIG. 11A is a plan view of a pattern of transmission image in a case where the workpiece pattern is a cut pattern.

FIGS. 11A and 11B show an example of the cut pattern of the workpiece being tested, wherein FIG. 11A shows a transmitted light image 220 of the cut pattern whereas FIG. 11B shows a reflected light image 240 of it. These transmitted and reflected images as derived from the same workpiece pattern are reverse to each other: in this sense, their mutual relationship is grosso modo similar to that of photographic positive and negative images. The transmitted image 220 of the cut pattern is shown to have a main pattern 12a and an assist pattern 12c. The reflected image 240 of cut pattern has a main pattern 12b and an assist pattern 12d. In the transmitted image 220 and reflected image 240, there is substantially no difference in size between the main patterns 12a and 12b; however, the assist pattern 12c is appreciably smaller in size than the assist pattern 12d. In this way, in the case of the cut assist pattern, the assist pattern 12c of the transmitted image 220 becomes smaller in size than the assist pattern 12d of reflected image 240 due to optical characteristics thereof. This makes it possible to certainly distinguish between these assist patterns 12c and 12d. In brief, as for the cut assist pattern, an image change due to the size of its transmitted image is larger than that of the reflected image.

The size ratio of the assist pattern images 12c and 12d of FIGS. 11A and 11B is dependent on the assist pattern size. Thus, obtaining this size ratio makes it possible to obtain the size of the assist pattern of interest.

Figure 12B:
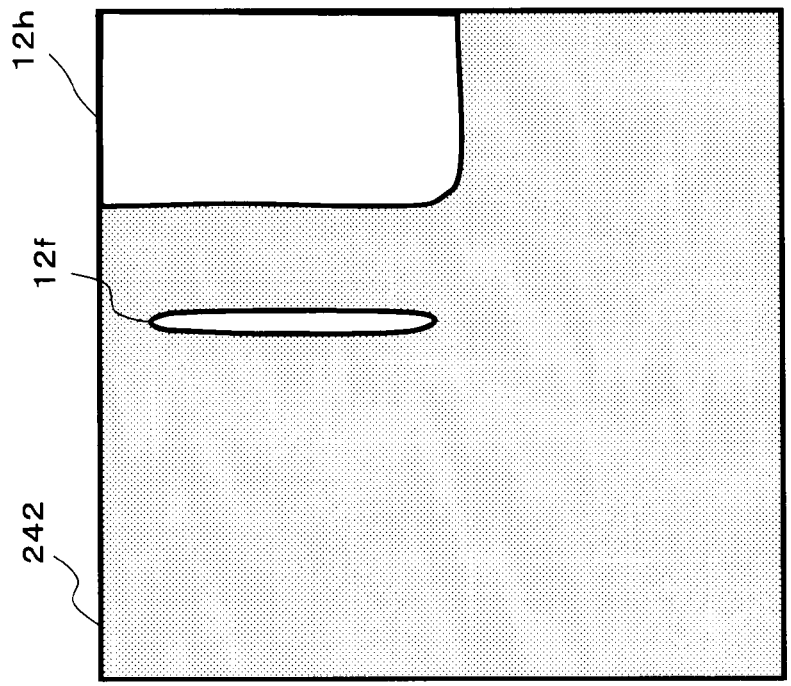
FIG. 12B shows a residue pattern of reflected image thereof.
Figure 12A:
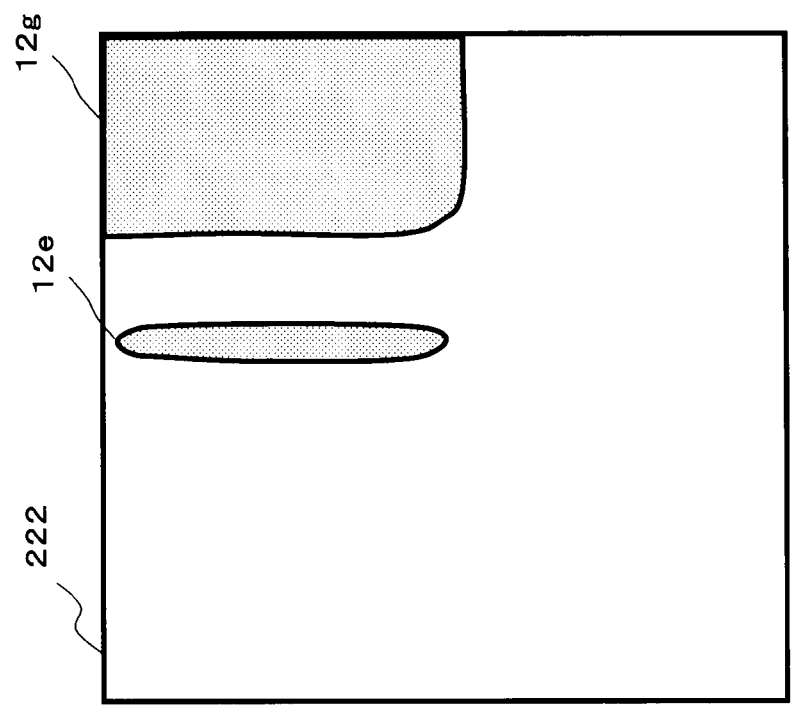
FIG. 12A is a plan view of a pattern of transmitted image in a case where the workpiece pattern is a residual pattern.

FIGS. 12A and 12B depict an example of the residue pattern of the workpiece being tested, wherein FIG. 12A shows a transmitted image 222 of the residue pattern whereas FIG. 12B shows a reflected image 242 thereof. The transmitted image 222 of residue pattern has an assist pattern 12e along with a main pattern 12g. The reflected image 242 of residue pattern has a main pattern 12h and an assist pattern 12f. In the transmitted image 222 and reflected image 242, there is substantially no difference in size between the main patterns 12g and 12h; however, the assist pattern 12f is less in size than the assist pattern 12e. In the case of such residue assist patterns, the assist pattern 12f of reflected image 242 becomes smaller in size than the assist pattern 12e of transmitted image 222 due to its optical characteristics. This makes it possible to distinguish between these assist patterns 12e and 12f. In short, regarding the residue assist pattern, an image change due to the size of reflected image is greater than that of the transmitted image.

The size ratio of the assist pattern images 12e and 12f in FIGS. 12A-12B is dependent on the assist pattern size. Thus it is possible to determine the assist pattern size by obtaining the size ratio.

The assist pattern discrimination condition 36 is obtainable by use of the representative image 32 and workpiece information 34, for causing the transmitted image to become larger in variation with respect to the size of the cut pattern while simultaneously causing the reflected image to stay less in variation with respect to the cut pattern size as can be seen from viewing FIGS. 11A and 11B or, alternatively, for causing the transmitted image to become smaller in variation with respect to the size of the residue pattern while at the same time forcing the reflected image to be large in variation with respect to the residue pattern size as shown in FIGS. 12A-12B. Based on this pattern discrimination condition feature, the workpiece inspection apparatus 10 of FIG. 1 is arranged to determine the patterns 12c-12f to be assist patterns and obtain desense area information 52 of these assist patterns. In such desense areas, judgment is done with the accuracy being lowered. By performing assist pattern discrimination in this way, it is possible to improve the accuracy of workpiece pattern inspection and increase inspection speed and throughputs.

In the workpiece inspection apparatus 10 of FIG. 3, when the patterns 12c-12f are decided to be assist patterns, the desense processing execution unit 60 is rendered operative to obtain final test result information 62 without regarding the defect-presumed portions as pattern defects. Thus, it is possible to improve the pattern inspection accuracy and also to increase the inspection speed and throughputs.

In the description above, those elements which are recited as "... units," "... circuits," "... processes," or "... steps" may be arranged by computer-executable software programs. Alternatively, these parts may be practically implemented by not only such software programs but also any possible combination of hardware and software modules. Still alternatively, they may be provided in various forms combined with firmware units. Alternatively, any possible combinations of these designs are employable. In the case of the parts being arranged by one or more programs, these programs are stored in a magnetic disk device, magnetic tape apparatus or recording media, such as a floppy diskette (FD), read-only memory (ROM) or like storage media.

This invention should not exclusively be limited to the illustrative embodiments stated supra. Although those components which are not directly necessary for explanation of this invention are omitted herein, such as apparatus configurations and control techniques or else, any required apparatus arrangements and control schemes are useable through appropriate choice on a case-by-case basis. Miscellaneously, every conceivable workpiece inspection apparatus which comprises the elements of this invention and which is design-alterable by those skilled in the art when the need arises is interpreted to be included within the scope of the invention.

What is claimed is:

1. A pattern discrimination device comprising:
an optical image acquisition unit configured to acquire both a transmissive image of a workpiece having a pattern and a reflective image of the workpiece pattern at a time; and
a specific pattern detection unit configured to distinctly detect a specific pattern from among pattern shapes of the transmissive and reflective images in conformity with a discrimination condition of the specific pattern,
wherein the discrimination condition of the specific pattern is based on the amount the size of the transmission image is smaller relative to the size of the reflection image for a cut pattern, or, alternatively, the amount the size of the reflection image is smaller relative to the size of the transmission image for a residue pattern.

2. The device according to claim 1, wherein the specific pattern is an assist pattern.

3. A workpiece inspection apparatus comprising:

an optical image acquisition unit configured to acquire both a transmissive image of a workpiece having a pattern and a reflective image of the workpiece pattern at a time;

a specific pattern detection unit configured to distinctly detect a specific pattern from among pattern shapes of the transmissive and reflective images in conformity with a discrimination condition of the specific pattern;

a specific inspection execution region setup unit configured to set the specific pattern in a specific inspection execution region; and a comparison judgment unit configured to perform, in the specific inspection execution region, pattern inspection of an optical image acquired by said optical image acquisition unit, wherein the discrimination condition of the specific pattern is based on the amount the size of the transmission image is smaller relative to the size of the reflection image for a cut pattern, or, alternatively, the amount the size of the reflection image is smaller relative to the size of the transmission image for a residue pattern.

4. The apparatus according to claim 3, wherein the specific pattern is an assist pattern and wherein the specific inspection execution region is an area with decreased sensitivity, called a desense area.

5. A workpiece inspection apparatus comprising:

an optical image acquisition unit configured to acquire both a transmissive image of a workpiece having a pattern and a reflective image of the workpiece pattern at a time;

a comparison judgment unit configured to perform pattern inspection of an optical image acquired by said optical image acquisition unit to thereby extract therefrom a portion which is deemed to be a defect;

a specific pattern detection unit configured to distinctly detect at the portion deemed to be the defect a specific pattern from among pattern shapes of the transmissive and reflective images in a way pursuant to a discrimination condition of the specific pattern; and a specific inspection execution unit configured to execute specific inspection if the portion deemed to be the defect is the specific pattern, wherein the discrimination condition of the specific pattern is based on the amount the size of the transmission image is smaller relative to the size of the reflection image for a cut pattern, or, alternatively, the amount the size of the reflection image is smaller relative to the size of the transmission image for a residue pattern.

6. The apparatus according to claim 5, wherein the specific pattern is an assist pattern and wherein the specific inspection is desense processing.

* * * * *